(12) United States Patent  (10) Patent No.: US 8,788,232 B2
Suzuno  (45) Date of Patent: Jul. 22, 2014

(54) ALTITUDE ESTIMATION APPARATUS, ALTITUDE ESTIMATION METHOD, AND PROGRAM

(75) Inventor: Satoshi Suzuno, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/813,044

(22) PCT Filed: May 31, 2012

(86) PCT No.: PCT/JP2012/003588
§ 371 (c)(1),
(2), (4) Date: Jan. 29, 2013

(87) PCT Pub. No.: WO2012/176383
PCT Pub. Date: Dec. 27, 2012

(65) Prior Publication Data
US 2013/0132019 A1  May 23, 2013

(30) Foreign Application Priority Data

Jun. 24, 2011  (JP) ................................. 2011-140286

(51) Int. Cl.
*G06F 17/00* (2006.01)
*A63B 71/00* (2006.01)
*G01C 21/16* (2006.01)
*A61B 5/11* (2006.01)

(52) U.S. Cl.
CPC .. *G01C 21/16* (2013.01); *A61B 5/11* (2013.01)
USPC ................. 702/94; 702/85; 482/54; 701/428; 701/480

(58) Field of Classification Search
CPC ...... G01C 21/16; G01C 21/32; G01C 21/005; G01C 21/26; A63B 24/006; A63B 2225/50; A63B 71/0622; A63B 5/11
USPC ............ 702/94; 701/428, 480, 213, 411, 420, 701/417, 416, 454, 431, 216, 427; 482/54, 482/8, 3, 1; 600/587
See application file for complete search history.

(56) References Cited

U.S. PATENT DOCUMENTS

| | | | |
|---|---|---|---|
| 6,512,976 B1 * | 1/2003 | Sabatino et al. | 701/469 |
| 6,761,064 B2 * | 7/2004 | Tsuji | 73/170.02 |
| 7,811,203 B2 * | 10/2010 | Unuma et al. | 482/8 |
| 8,082,098 B2 * | 12/2011 | Fukuda et al. | 701/31.4 |

(Continued)

FOREIGN PATENT DOCUMENTS

| | | |
|---|---|---|
| EP | 2 299 241 A2 | 3/2011 |
| JP | 10-168810 | 6/1998 |

(Continued)

OTHER PUBLICATIONS

PCT Written Opinion of the International Searching Authority dated Jun. 24, 2011 (PCT/JP2012/003588).

(Continued)

*Primary Examiner* — Carol S Tsai
(74) *Attorney, Agent, or Firm* — Oblon, Spivak, McClelland, Maier & Neustadt, L.L.P.

(57) ABSTRACT

An information processing apparatus that acquires estimated altitude data corresponding to a position based on detection information detected by a sensor at or near the position, and corrects altitude data associated with the position based on the estimated altitude data.

14 Claims, 11 Drawing Sheets

(56) References Cited

U.S. PATENT DOCUMENTS

| | | | |
|---|---|---|---|
| 8,260,552 B2 * | 9/2012 | Jeerage et al. | 701/480 |
| 8,271,192 B2 * | 9/2012 | Jung et al. | 701/428 |
| 2007/0072158 A1 * | 3/2007 | Unuma et al. | 434/247 |
| 2010/0100318 A1 * | 4/2010 | Jung et al. | 701/211 |

FOREIGN PATENT DOCUMENTS

| | | |
|---|---|---|
| JP | 10-168810 A | 6/1998 |
| JP | 2004-93632 A | 3/2004 |
| JP | 2004-325777 | 11/2004 |
| JP | 2004-325777 A | 11/2004 |
| JP | 2009-162740 | 7/2009 |
| JP | 2009-229204 | 10/2009 |
| JP | 2010-25598 | 2/2010 |
| JP | 2010-43938 | 2/2010 |
| JP | 2010-113365 | 5/2010 |
| JP | 2010-113365 A | 5/2010 |
| JP | 2011-64592 | 3/2011 |
| JP | 2011-64592 A | 3/2011 |
| WO | 2008/140147 A1 | 11/2008 |

OTHER PUBLICATIONS

European Search Report issued in European Patent Application No. 12803213.3 on May 9, 2014.

* cited by examiner

Fig. 8

| SENSOR TYPE | ACQUIRABLE INFORMATION | UP/DOWN DETERMINATION METHOD |
|---|---|---|
| GPS | ALTITUDE (ERROR NUMBER M) * ALSO, BASED ON RECEPTION STATUS OF GPS | DETERMINE ROUGH UP/DOWN BASED ON ALTITUDE VALUE |
| ACCELERATION SENSOR | CHANGE IN SPEED CHANGE IN SLOPE | DETERMINE UP/DOWN BASED ON CHANGE IN SPEED OR SLOPE (UPHILL ROAD IF SPEED IS INCREASED, DOWNHILL ROAD IF SPEED IS DECREASED) |
| GYRO | CHANGE IN ANGULAR VELOCITY | DETERMINE UP/DOWN BASED ON CHANGE IN ANGULAR VELOCITY (WHEN CHANGE IS LARGE, IT IS ESTIMATED THAT USER PEDALS BICYCLE AND BODY OF BICYCLE IS SHAKEN, THUS UPHILL ROAD. WHEN CHANGE IS SMALL, DOWNHILL ROAD) |
| GEOMAGNETIC SENSOR | CHANGE IN AZIMUTH | DETERMINE UP/DOWN BASED ON CHANGE IN AZIMUTH (WHEN CHANGE IS LARGE, IT IS ESTIMATED THAT USER PEDALS BICYCLE AND BODY OF BICYCLE IS SHAKEN, THUS UPHILL ROAD. WHEN CHANGE IS SMALL, DOWNHILL ROAD) |
| BAROMETRIC PRESSURE SENSOR | ALTITUDE | DETERMINE UP/DOWN BASED ON ALTITUDE VALUE |

ALTITUDE ESTIMATION APPARATUS, ALTITUDE ESTIMATION METHOD, AND PROGRAM

TECHNICAL FIELD

The present disclosure relates to an altitude estimation apparatus, an altitude estimation method, and a program.

BACKGROUND ART

Recently, navigation systems, represented by car navigation systems, have been propagated. Car navigation systems perform display of a current position or route guidance to a destination when an automobile travels. The display of a current position or the route guidance to a destination is normally performed on a map displayed on a screen of a navigation terminal. Furthermore, the route guidance may be performed through sound.

As an example of the navigation system, a navigation terminal for a bicycle or walk has also been known in recent years. The navigation terminal for a bicycle or walk may perform route guidance by giving priority to a road with a gentle slope with reference to altitude data in addition to map data. Here, the altitude data, for example, may be acquired from a plurality of images, which have been photographed from the upper air by an airplane, an artificial satellite and the like, through a stereo image process, or may also be acquired using a method of measuring the position and altitude of each point by irradiating laser from an airplane or a satellite using a laser profiler, as disclosed in Patent Literature 1.

CITATION LIST

Patent Literature

PTL 1: Patent Literature 1: Japanese Patent Application Laid-Open No. 2004-93632

SUMMARY

Technical Problem

However, the altitude data acquired using the above method may be different from actual altitude.

According to a first exemplary embodiment, the disclosure is directed to an information processing apparatus comprising: a processor that acquires estimated altitude data corresponding to a position based on detection information detected by a sensor at or near the position; and corrects altitude data associated with the position based on the estimated altitude data.

According to another exemplary embodiment, the disclosure is directed to an information processing apparatus comprising: a processor that estimates altitude data corresponding to a position based on detection information detected by a sensor at or near the position; and computes altitude correction information associated with the position based on the estimated altitude data.

According to another exemplary embodiment, the disclosure is directed to an information processing apparatus comprising: a processor that determines a position of the information processing apparatus; a sensor that detects detection information corresponding to the information processing apparatus; an interface that transmits the position and the detection information to another information processing apparatus, which estimates altitude data corresponding to the position based on the detection information and corrects stored altitude data associated with the position based on the estimated altitude data.

According to another exemplary embodiment, the disclosure is directed to an information processing apparatus comprising: a processor that determines a position of the information processing apparatus; an interface that transmits the position to another information processing apparatus, and receives, from the another apparatus, altitude data corresponding to the position, the altitude data having been corrected based on estimated altitude data corresponding to the position, which was estimated based on detection information detected by a sensor at or near the position.

Advantageous Effects of Invention

According to the present disclosure as described above, it is possible to improve the accuracy of altitude data.

BRIEF DESCRIPTION OF DRAWINGS

FIG. 8 is a diagram illustrating a method by which the altitude estimation server according to the first embodiment of the present disclosure determines up/down from sensor information.

DESCRIPTION OF EMBODIMENTS

Figure 1:
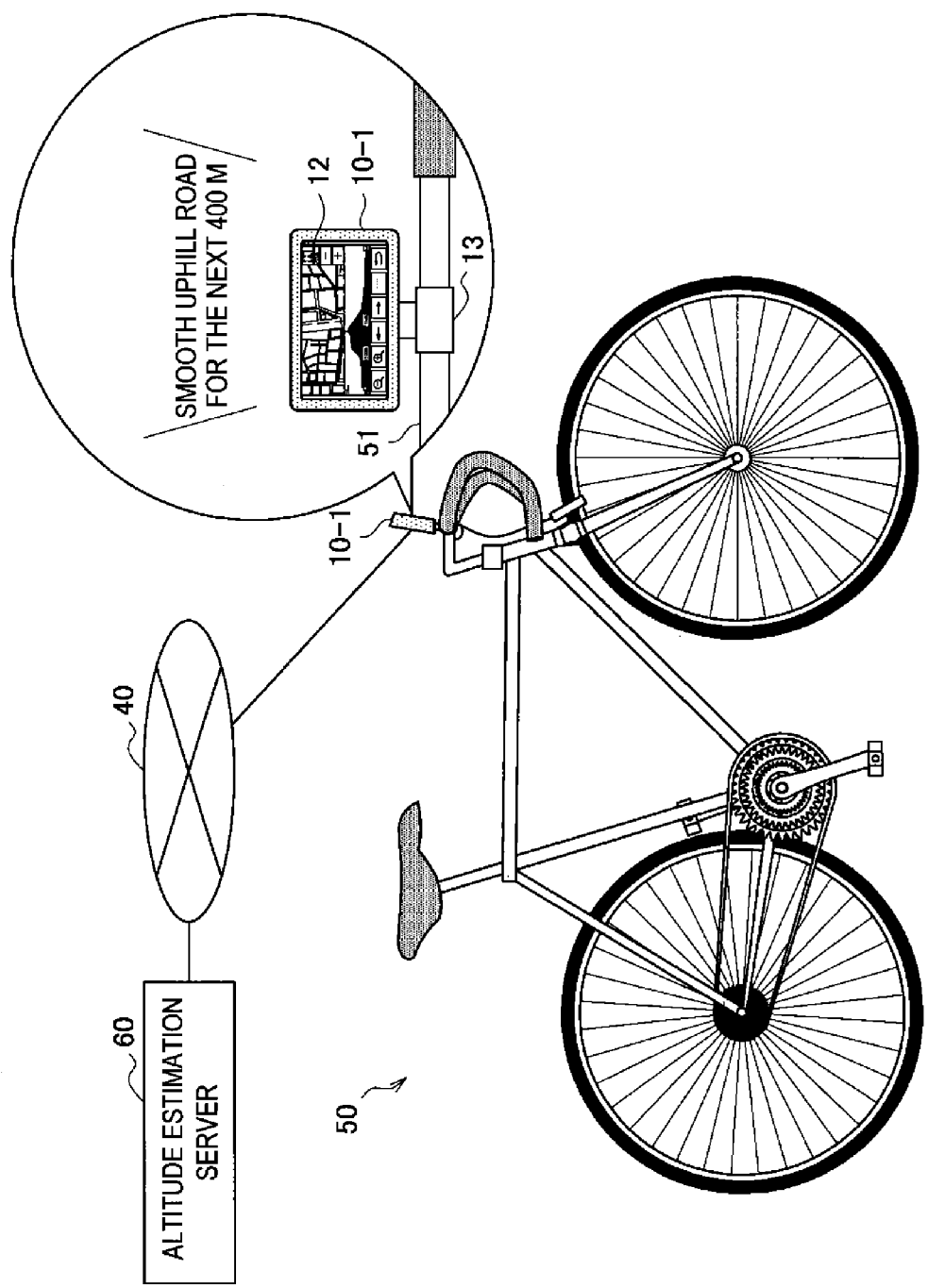
FIG. 1 is an overall diagram illustrating a navigation system according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Furthermore, the present disclosure will be described in the following order.

1. First embodiment
2. Second embodiment
3. Third embodiment
4. Conclusion

Technology according to the present disclosure described herein may be implemented in various forms such as the above items "1. First embodiment" to "3. Third embodiment." Furthermore, a navigation terminal 10-2 or 10-3 or an altitude estimation server 60 according to each embodiment is an altitude estimation apparatus including (1) an estimation unit (an altitude estimation unit 620 and an altitude estimation unit 151) for estimating altitude data of a position on a movement route using detection information detected by a sensor on the movement route, and (2) a correction unit (an altitude correction unit 630 and an altitude correction unit 152) for correcting altitude data, which has been set to be associated with the position on the movement route, based on the altitude data estimated by the estimation unit.

1. FIRST EMBODIMENT

In the first embodiment, an altitude estimation apparatus according to the present disclosure is applied to the altitude estimation server 60. Furthermore, a navigation terminal 10-1 is used as a mobile terminal. Hereinafter, a navigation system according to the first embodiment will be described, which includes the altitude estimation server 60 and the navigation terminal 10-1.

1-1. Outline of Navigation System (Entire Configuration)

FIG. 1 is a diagram illustrating an entire configuration of a navigation system according to the first embodiment. As illustrated in FIG. 1, the navigation system according to the first embodiment includes the navigation terminal 10-1 attached to a bicycle 50, and the altitude estimation server 60, wherein the navigation terminal 10-1 and the altitude estimation server 60 are connected to each other through a network 40.

As illustrated in FIG. 1, the navigation terminal 10-1, for example, is realized by a personal navigation device (PND). Furthermore, as illustrated in FIG. 1, the navigation terminal 10-1 is attached to a handle 51 of the bicycle 50 through a cradle 13 for a bicycle. Preferably, an attachment position is a position at which eyes of a user are turned in a small range when the user views a display unit 12 of the navigation terminal 10-1 while riding the bicycle 50.

The navigation terminal 10-1 has a navigation function of guiding a route to a destination. For example, when a user rides the bicycle 50, it is possible for the navigation terminal 10-1 to guide a route by selecting a road with good conditions. Furthermore, it is possible for the navigation terminal 10-1 to search for a route as a route candidate through guidance of a road along which a vehicle such as an automobile may not run. Moreover, it is possible for the navigation terminal 10-1 to display information on a traveling speed, a traveling distance, calorie consumption and the like of a bicycle. In addition, the navigation terminal 10-1 may have a plurality of operation modes including an onboard mode and a walking mode, in addition to a bicycle mode in which route guidance for bicycle traveling is performed.

Furthermore, it is possible for the navigation terminal 10-1 according to the present embodiment to output sensor information detected during the travel of the bicycle to the altitude estimation server 60, and to acquire altitude data corrected in the altitude estimation server 60.

(External Appearance of Navigation Terminal)

Figure 2:
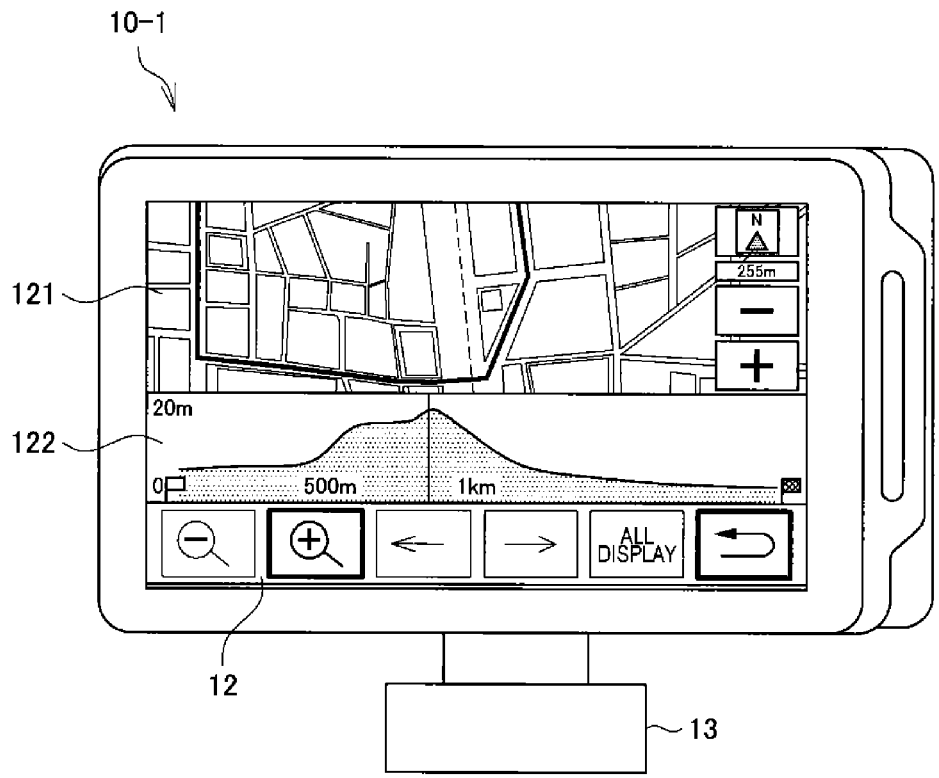
FIG. 2 is a diagram illustrating an external appearance of a navigation terminal according to the first embodiment of the present disclosure.

Next, an external appearance of the navigation terminal 10-1 will be described with reference to FIG. 2. FIG. 2 is a diagram illustrating the external appearance of the navigation terminal 10-1 that displays an information providing screen. As illustrated in FIG. 2, a housing of the navigation terminal 10-1 is held by a bicycle through the cradle 13 attachable to the handle of the bicycle. The navigation terminal 10-1 is easily attachable to or detachable from the cradle 13.

Furthermore, the navigation terminal 10-1 is provided with the display unit 12 that displays an image including the information providing screen for providing various types of information through a front surface thereof. The navigation terminal 10-1 has a function of acquiring its own current position information, and stores the map data and altitude data acquired from the altitude estimation server 60. Consequently, as illustrated in FIG. 2, it is possible for the navigation terminal 10-1 to display a map screen 121 and an altitude screen 122 on the display unit 12, wherein the map screen 121 displays current position information superimposed on a map, and the altitude screen 122 displays a change in the altitude of a route through a graph.

(For Information Providing Screen)

Figure 3:
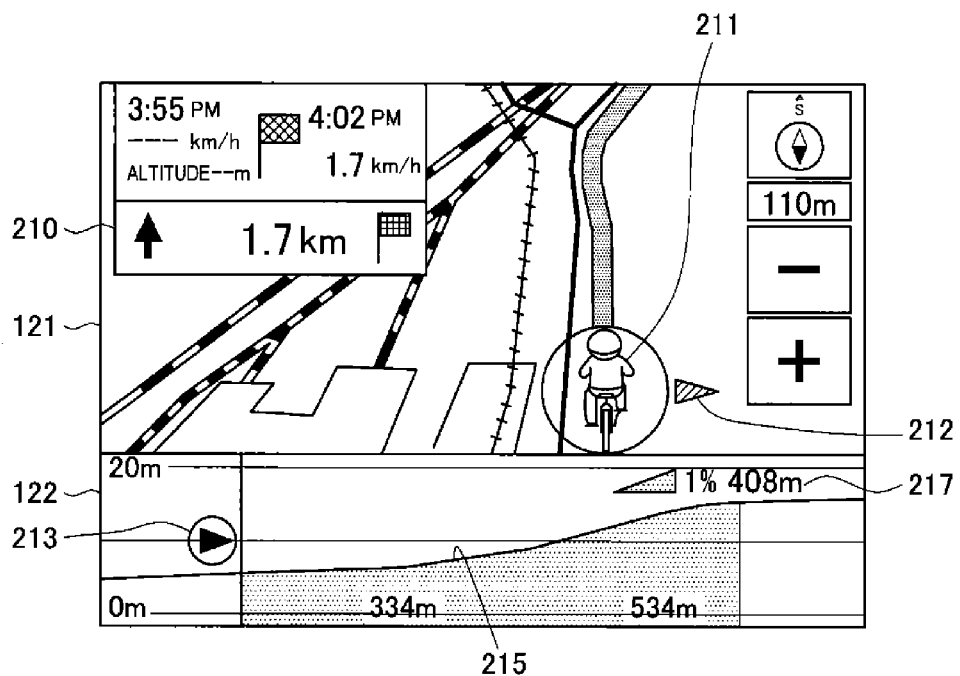
FIG. 3 is a diagram illustrating another example of an information providing screen displayed on a navigation terminal.

Next, the information providing screen displayed on the navigation terminal 10-1 according to the present embodiment will be described with reference to FIG. 3. FIG. 3 is a diagram illustrating another example of the information providing screen displayed on the navigation terminal 10-1. As illustrated in FIG. 3, the information providing screen includes the map screen 121 and the altitude screen 122.

The map screen 121 is a screen on which route guidance information display 210 and a bicycle icon 211 are superimposed on a map. The navigation terminal 10-1 performs route guidance using the map screen 121. Furthermore, an arrow 212 displayed on a circle surrounding the bicycle icon 211 illustrated in FIG. 3 indicates the direction of a destination.

Furthermore, the altitude screen 122 includes a current position icon 213, an altitude graph 215 indicating a change in altitude, and a slope information display 217. Through the altitude graph 215, it is possible for the navigation terminal 10-1 to provide a user with information whether a road to be traveled is flat or uphill or downhill slope is severe. Furthermore, the slope information display 217 illustrated in FIG. 3 indicates that an uphill road with a slope of 1% continues for 408 m from a current location. The altitude screen 122 is generated based on altitude data.

Figure 4:
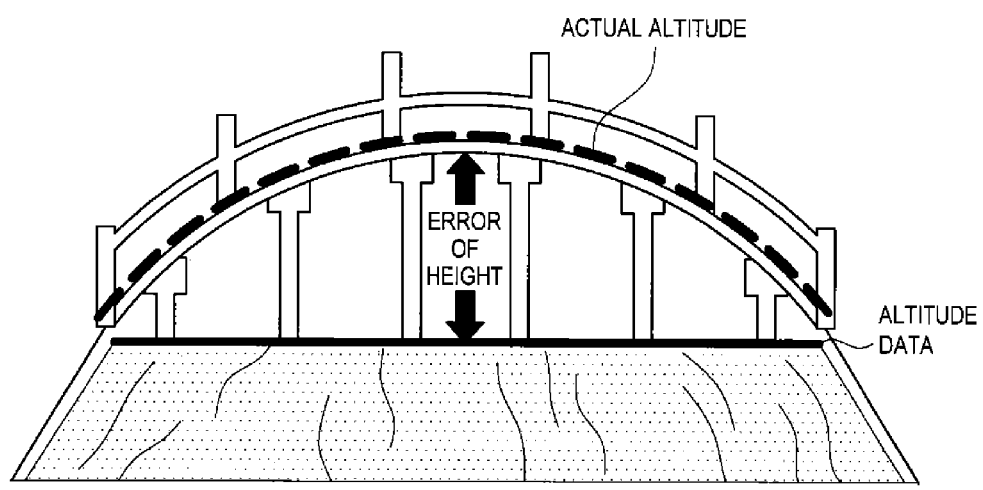
FIG. 4 is a diagram for explaining a case where there is a difference between altitude data and actual altitude.

Here, since the altitude data is acquired in advance by laser measurement or image measurement, the height of a building such as a bridge or an elevated construction may not be correctly calculated. For example, as illustrated in FIG. 4, as altitude data of a bridge built across a river, the height of a water surface may be erroneously calculated. In this case, since a bridge actually having a slope with an arch shape is displayed on an altitude screen or a 3D map screen as a flat road in the navigation terminal 10-1, a user may feel inconvenienced. Furthermore, when actual altitude is different from altitude data, it is difficult for the navigation terminal 10-1 to accurately perform route search according to slope.

In this regard, in the navigation system according to the present embodiment, the altitude estimation server 60 corrects the altitude data based on sensor information actually acquired by the navigation terminal 10-1 during the travel, resulting in the improvement of the accuracy of the altitude data.

So far, the outline of the navigation system according to the present embodiment has been described. Next, the navigation terminal 10-1 and the altitude estimation server 60, which constitute the navigation system, will be described, respectively.

1-2. Configuration of Navigation Terminal

Figure 5:
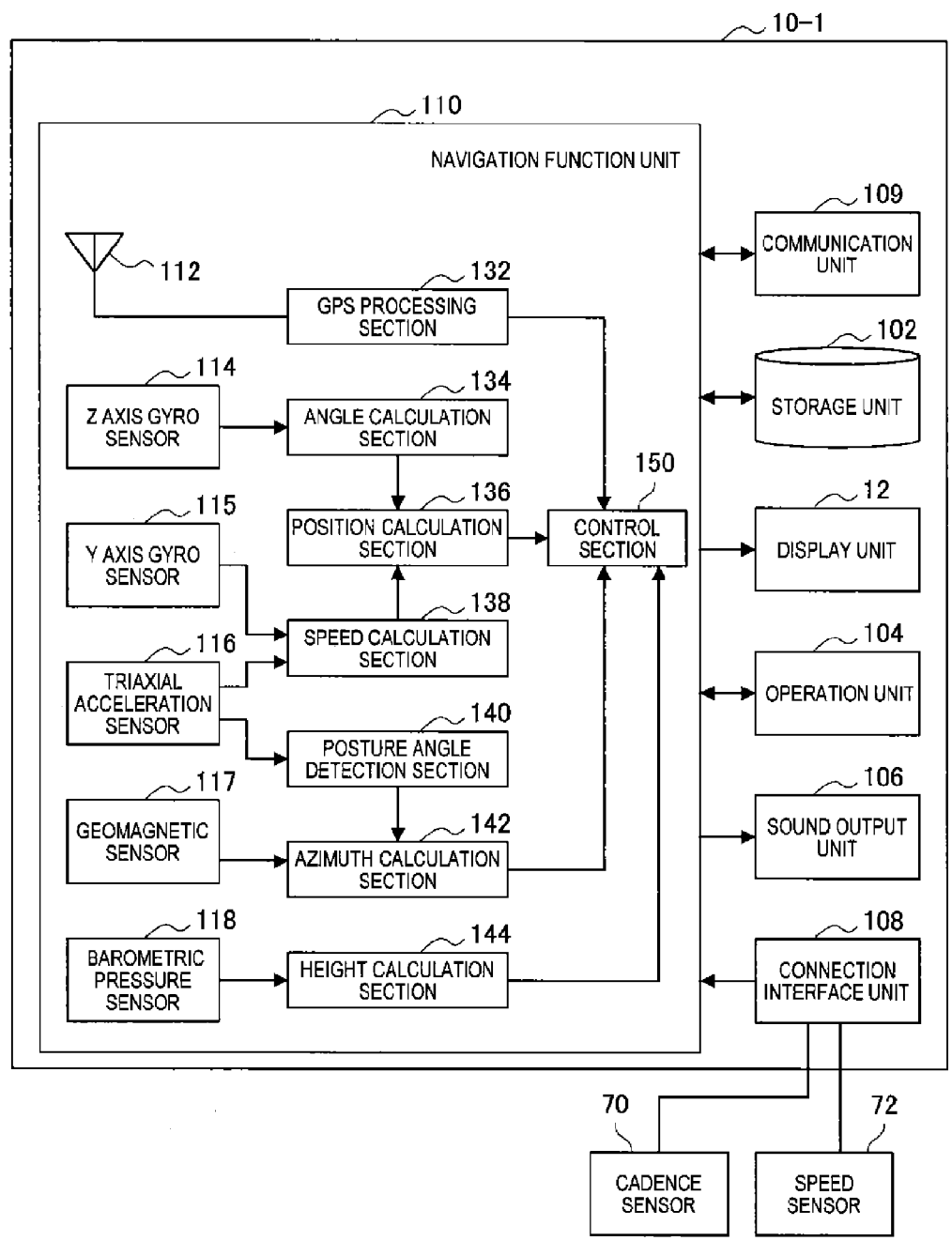
FIG. 5 is a block diagram illustrating a configuration of the navigation terminal according to the first embodiment of the present disclosure.

FIG. 5 is a block diagram illustrating a configuration of the navigation terminal 10-1 according to the present embodiment. As illustrated in FIG. 5, the navigation terminal 10-1 mainly includes the display unit 12, a storage unit 102, an operation unit 104, a sound output unit 106, a connection interface unit 108, a communication unit 109, and a navigation function unit 110.

The navigation function unit 110 includes a GPS antenna 112, a Z axis gyro sensor 114, a Y axis gyro sensor 115, a triaxial acceleration sensor 116, a geomagnetic sensor 117, a barometric pressure sensor 118, a GPS processing section 132, an angle calculation section 134, a position calculation section 136, a speed calculation section 138, a posture angle detection section 140, an azimuth calculation section 142, a height calculation section 144, and a control section 150. As illustrated in FIG. 5, the navigation terminal 10-1 includes the various sensors (the GPS antenna 112, the Z axis gyro sensor 114, the Y axis gyro sensor 115, the triaxial acceleration sensor 116, the geomagnetic sensor 117, and the barometric pressure sensor 118). However, the navigation terminal according to the present disclosure is not limited to the configuration illustrated in FIG. 5. For example, the navigation terminal may have at least one of the sensors.

The display unit 12, for example, is a display device for outputting a screen in which information indicating a current position is superimposed on map data. The display unit 12, for example, may also be a display device such as a liquid crystal display (LCD) or organic electroluminescence (EL) display.

The storage unit 102 is a storage medium for storing a program for operating the navigation terminal 10-1, map data, altitude data and the like. The storage unit 102 according to the present embodiment stores the map data and the altitude data acquired from the altitude estimation server 60.

In addition, the display unit 102, for example, may also be a storage medium such as a nonvolatile memory including a flash ROM (or a flash memory), an electrically erasable programmable ROM (EEPROM), an erasable programmable ROM (EPROM) and the like, a magnetic disk including a hard disk, a disk-type magnetic disk and the like, an optical disc including a compact disc (CD), a digital versatile disc recordable (DVD-R), a Blu-ray disc (BD, a registered trademark) and the like, or a magneto optical (MO) disc.

The operation unit 104 receives a user's operation instruction and outputs operation content thereof to the navigation function unit 110. The user's operation instruction, for example, may include setting of a destination, enlargement and reduction of a map, sound guidance setting, screen display setting and the like. The operation unit 104 may also be a touch screen integrally provided with the display unit 12. Otherwise, the operation unit 104 may also be a physical configuration, which is provided separately from the display unit 12, such as a button, a switch, or a lever. Furthermore, the operation unit 104 may also be a signal reception unit for detecting a signal indicating a user's operation instruction transmitted from a remote controller.

The sound output unit 106 is an output device for outputting sound data, and for example, may be a speaker, an earphone, a headphone and the like. The sound output unit 106, for example, outputs sound guidance related to navigation. It is possible for a user to recognize a route to be traveled by listening to the sound guidance without viewing the display unit 12. Furthermore, it is possible for the sound output unit 106 according to the present embodiment to output slope information on a route to be traveled by the bicycle 50 from a current location through sound.

The connection interface unit 108 is an interface for a connection to a speed sensor 72 and a cadence sensor 70. The connection interface unit 108 receives a speed pulse signal which is output from the speed sensor 72, and inputs received information to the control section 150. Furthermore, the connection interface unit 108 receives a cadence pulse signal which is output from the cadence sensor 70, and inputs received information to the control section 150.

The communication unit 109 is an interface with the altitude estimation server 60, and has functions as a transmission unit for transmitting information to the altitude estimation server 60, and a reception unit for receiving information from the altitude estimation server 60. For example, the communication unit 109 transmits information, which is detected by various sensors of the navigation terminal 10-1 during the travel of the bicycle, to the altitude estimation server 60. Furthermore, the communication unit 109 acquires the map data and the altitude data from the altitude estimation server 60.

It is possible for the GPS antenna 112 to receive GPS signals from a plurality of GPS satellites, and input the received GPS signals to the GPS processing section 132. In addition, the received GPS signals include orbital data indicating the orbit of the GPS satellite, a signal reception time and the like.

The GPS processing section 132 calculates position information indicating the current position of the navigation terminal 10-1 based on a plurality of GPS signals which are input from the GPS antenna 112, and supplies the calculated position information to the control section 150. In detail, the GPS processing section 132 calculates the position of each GPS satellite from orbital data obtained by demodulating the plurality of GPS signals, and calculates the distance to the navigation terminal 10-1 from each GPS satellite from the difference between a transmission time and a reception time of the GPS signal. Then, the GPS processing section 132 calculates a current three-dimensional position based on the calculated position of each GPS satellite and the calculated distance to the navigation terminal 10-1 from each GPS satellite.

The navigation function unit 110 has a relative position acquisition function using various sensors, in addition to an absolute position acquisition function using the GPS antenna 112 and the GPS processing section 132. Information on a relative position may also be used in a situation in which an absolute position may not be acquired, that is, a situation in which the navigation terminal 10-1 is in a position where a GPS signal may not be received. Furthermore, the information on the relative position may also be combined with information on the absolute position.

Figure 6:
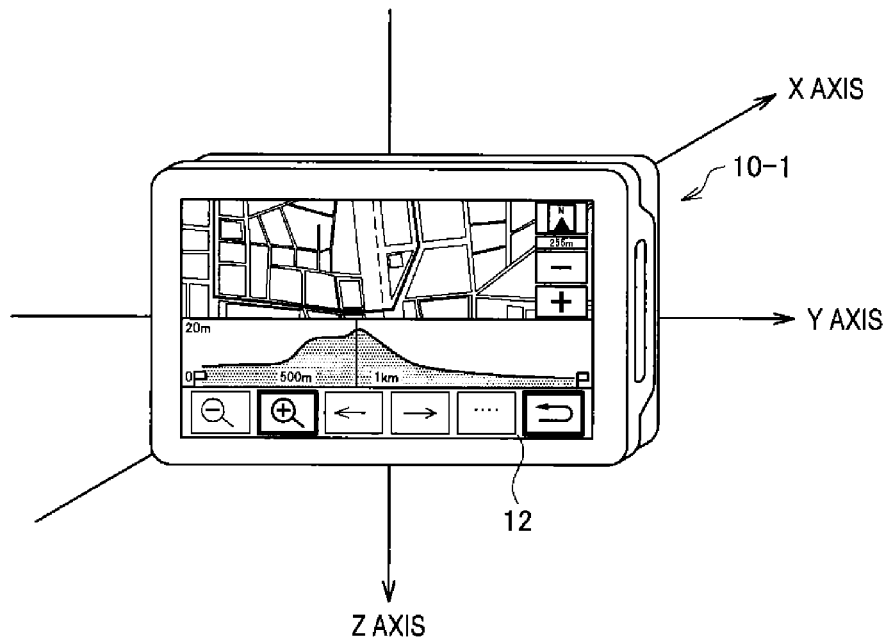
FIG. 6 is a diagram for explaining a coordinate system in the vicinity of the navigation terminal according to the first embodiment of the present disclosure.

The Z axis gyro sensor 114 has a function of detecting a yaw rate $O_z$ as a voltage value, which is a velocity (an angular velocity) at which a rotation angle around a Z axis changes when the navigation terminal 10-1 runs along a curved road. The Z axis gyro sensor 114, for example, detects the yaw rate at a sampling frequency of 50 Hz, and inputs data indicating the detected yaw rate to the angle calculation section 134. In addition, as illustrated in FIG. 6, the Z axis corresponds to a vertical direction. An X axis corresponds to a travel direction of the navigation terminal 10-1 and a Y axis corresponds to a horizontal direction perpendicular to the X axis.

The angle calculation section 134 calculates an angle T when the navigation terminal 10-1 has run along a curved road by multiplying a sampling period (for example, 0.02 s) by the yaw rate $O_z$ which is input from the Z axis gyro sensor 114, and inputs angular data indicated by the angle T to the position calculation section 136.

The Y axis gyro sensor 115 has a function of detecting a pitch rate $O_y$ as a voltage value, which is an angular velocity around the Y axis. The Y axis gyro sensor 115, for example, detects the pitch rate at a sampling frequency of 50 Hz, and inputs data indicating the detected pitch rate to the speed calculation section 138.

The triaxial acceleration sensor 116 has a function of detecting acceleration $A_x$ along the X axis, acceleration $A_y$ along the Y axis, and acceleration $A_z$ along the Z axis as voltage values, respectively. The triaxial acceleration sensor 116, for example, detects the acceleration $A_x$, the acceleration $A_y$, and the acceleration $A_z$ at a sampling frequency of 50 Hz, and inputs data indicating the detected acceleration to the speed calculation section 138 and the posture angle detection section 140.

The speed calculation section 138, for example, calculates velocity V with respect to a travel direction 50 times each second by dividing the acceleration $A_z$ along the Z axis, which is input from the triaxial acceleration sensor 116, by the pitch rate $O_y$ which is input from the Y axis gyro sensor 115, and inputs the calculated velocity V to the position calculation section 136.

The position calculation section 136 has a function of calculating position information on a current position based on the velocity V calculated by the speed calculation section 138 and the angle T calculated by the position calculation section 136. In detail, the position calculation section 136 calculates a variation between a position in the previous calculation and the current position based on the velocity V and the angle T. Then, the position calculation section 136 calculates the position information on the current position from the variation and the position in the previous calculation, and supplies the position information on the current position to the control section 150.

The posture angle detection section 140 generates posture angle data indicating a posture angle of the navigation terminal 10-1 by performing a predetermined posture angle detection process based on the acceleration data $A_x$, $A_y$, and $A_z$ which is input from the triaxial acceleration sensor 116, and inputs the posture angle data to the azimuth calculation section 142.

The geomagnetic sensor 117 detects geomagnetism $M_x$, $M_y$, and $M_z$ in X, Y, and Z axis directions as voltage values, respectively. The geomagnetic sensor 117 inputs the detected geomagnetic data $M_x$, $M_y$, and $M_z$ to the azimuth calculation section 142.

The azimuth calculation section 142 performs a predetermined correction process with respect to the geomagnetic data $M_x$, $M_y$, and $M_z$ which is input from the geomagnetic sensor 117, and generates azimuth data indicating the azimuth of the navigation terminal 10-1 based on the corrected geomagnetic data and the posture angle data which is input from the posture angle detection section 140. The azimuth calculation section 142 supplies the generated azimuth data to the control section 150.

That is, the geomagnetic sensor 117, the triaxial acceleration sensor 116, the posture angle detection section 140, and the azimuth calculation section 142 serve as a so-called electronic compass, and generate azimuth data. When the navigation terminal 10-1 is mainly used after being detached from the cradle 13 (for example, when the navigation terminal 10-1 is used for walking), it is possible for the control section 150 to provide a user with map data, which is displayed according to the direction of the navigation terminal 10-1, using the azimuth data. In addition, when the navigation terminal 10-1 is used in an onboard mode, it is possible for the control section 150 to associate a road on map data from the route of an own bicycle position with the own bicycle position, and to provide a user with map data according to the direction of the navigation terminal 10-1 based on the azimuth of the map. Otherwise, it is possible for the control section 150 to calculate the direction of the navigation terminal 10-1 from acquired GPS azimuth, and to provide a user with map data according to the direction of the navigation terminal 10-1.

The barometric pressure sensor 118 has a function of detecting peripheral barometric pressure as a voltage value. The barometric pressure sensor 118, for example, detects barometric pressure at a sampling frequency of 50 Hz, and inputs detected barometric pressure data to the height calculation section 144.

The height calculation section 144 calculates the height of the navigation terminal 10-1 based on the barometric pressure data which is input from the barometric pressure sensor 118, and supplies calculated height data to the control section 150.

With such a configuration, it is possible for the control section 150 to acquire the current position information from the GPS processing section 132 or the position calculation section 136, azimuth of the navigation terminal 10-1 from the azimuth calculation section 142, and the height of the navigation terminal 10-1 from the height calculation section 144. Here, the control section 150 may use information on the acquired position as is. However, the control section 150 may also perform various correction processes. For example, a typical example of the correction process may include a map matching process. The map matching process uses map information in order to correct an error of position information. Through the map matching process, a corresponding road on a map is searched for from a change in the position information, correct position information is estimated, and the position information is corrected based on the estimation.

Hereinafter, the detailed functional configuration of the control section 150 will be described. The control section 150 mainly has a navigation function of guiding a route to a point set as a destination. In order to perform the navigation function, the control section 150 has a function of acquiring current position information, a function of correcting the acquired position information, a function of acquiring position information of a designated point based on operation information by the operation unit 104, a function of searching for a route based on map information, and the like. Then, the control section 150 guides a user to reach a destination based on the searched route and the acquired position information. In addition, it is possible for the control section 150 according to the present embodiment to perform route search in consideration of the slope of a route based on altitude data. For example, it is possible for the control section 150 to perform route search excluding a sloping road, route search by adding priority to a sloping road for the purpose of training, and the like.

Furthermore, the control section 150 has an operation mode switching function of switching an operation mode of the navigation terminal 10-1. For example, the control section 150 acquires information on a user's operation for an operation mode selection screen displaying an operation mode item, and switches the operation mode of the navigation terminal 10-1 based on the operation information. Here, a selectable operation mode includes an onboard mode selected when the navigation terminal 10-1 is installed in an automobile, a bicycle mode selected when the navigation terminal 10-1 is installed in a bicycle, a walk mode selected when a user goes on foot, and the like.

Furthermore, the control section 150 has a display control function of displaying the content of a display screen displayed on the display unit 12. For example, when the navigation terminal 10-1 operates in the bicycle mode, the control section 150, for example, may allow the altitude screen 122 illustrated in FIG. 2 or FIG. 3 to be displayed.

Furthermore, the control section 150 according to the present embodiment sends information, which is detected by the various sensors (the GPS antenna 112, the Z axis gyro sensor 114, the Y axis acceleration sensor 115, the triaxial acceleration sensor 116, the geomagnetic sensor 117, and the barometric pressure sensor) during the travel, to the altitude estimation server 60 from the communication unit 109.

As described above, the navigation terminal 10-1 transmits the information detected by the various sensors during the travel to the altitude estimation server 60. Furthermore, the navigation terminal 10-1 generates the information providing screen based on the map data and the altitude data acquired from the altitude estimation server 60, and displays the information providing screen on the display unit 12. Route guidance is performed using the altitude screen included in the information providing screen displayed by the navigation terminal 10-1, so that the navigation terminal 10-1 can perform route guidance according to the altitude of a route. Next, the altitude estimation server 60 that provides altitude data to the navigation terminal 10-1 will be described.

1-3. Altitude Estimation Server (Configuration)

Figure 7:
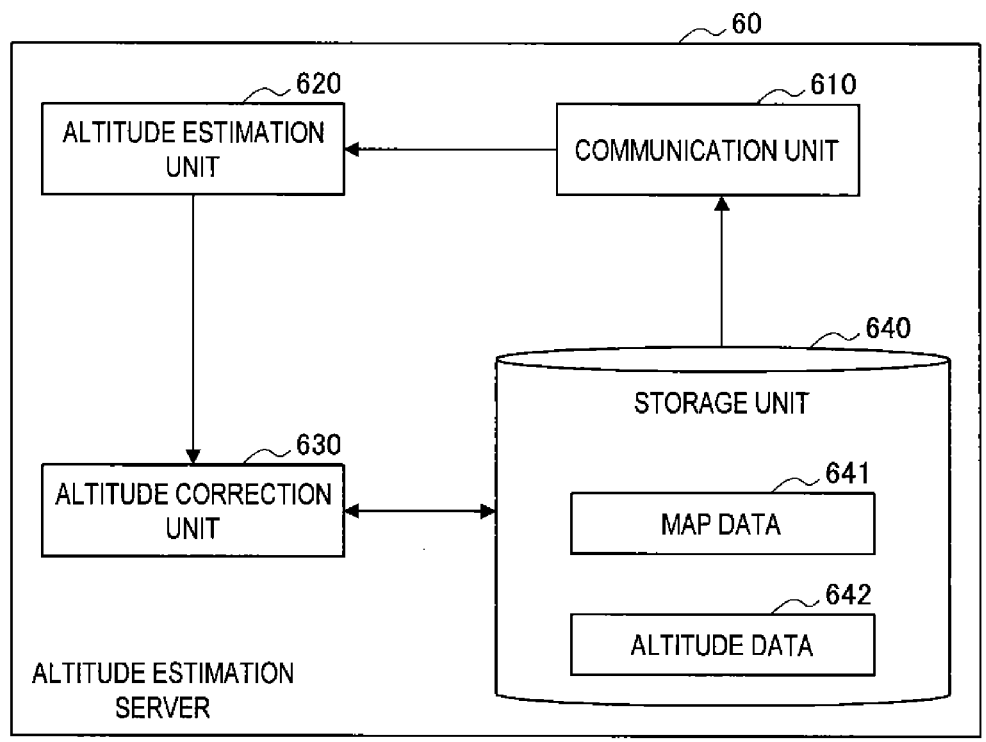
FIG. 7 is a block diagram illustrating a configuration of an altitude estimation server according to the first embodiment of the present disclosure.

FIG. 7 is a block diagram illustrating a configuration of the altitude estimation server 60 according to the present embodiment. As illustrated in FIG. 7, the altitude estimation server 60 includes a communication unit 610, an altitude estimation unit 620, an altitude correction unit 630, and a storage unit 640.

The communication unit 610 is an interface with a plurality of navigation terminals 10-1, and has a function as a transmission unit for transmitting information to the plurality of navigation terminals 10-1, and a reception unit for receiving information from the plurality of navigation terminals 10-1. For example, the communication unit 610 receives information, which is detected by the various sensors during the travel of the bicycle, from the navigation terminals 10-1. The communication unit 610 transmits the information of the various sensors, which is received from the navigation terminals 10-1, to the altitude estimation unit 620. Furthermore, the communication unit 610 transmits map data 641 and altitude data 642 stored in the storage unit 640 to the navigation terminals 10-1.

The altitude estimation unit 620 estimates altitude data based on the information of the various sensors, which is output from the communication unit 610. In detail, the altitude estimation unit 620 determines a change (up/down) in the altitude of a route based on the information of various sensors, and calculates altitude data of a point with up/down as a correction value. Hereinafter, a detailed up/down determination method in each sensor will be described with reference to FIG. 8.

FIG. 8 is a diagram illustrating a sensor type, information acquirable from sensors, and a method of determining up/down from the information. The information acquirable from the sensor type "GPS" illustrated in FIG. 8 includes three-dimensional position information calculated by the GPS processing section 132 provided in the navigation terminal 10-1 as described above. Thus, the altitude estimation unit 620 determines up/down based on altitude data included in the three-dimensional position information, and calculates a correction value of a point with up/down. However, since several meters of error may occur due to the reception situation of the GPS antenna 112, the altitude estimation unit 620 may determine rough up/down based on the three-dimensional position information, and calculate a correction value.

Furthermore, the information acquirable from the sensor type "acceleration sensor" illustrated in FIG. 8 includes the data indicating acceleration detected by the triaxial acceleration sensor 116 provided in the navigation terminal 10-1 as described above. Thus, the altitude estimation unit 620 extracts a change in a slope of a graph indicating a change in speed and a change in acceleration at each time from the data indicating acceleration, determines up/down based on the change in the speed or the slope, and calculates a correction value of a point with up/down. For example, the altitude estimation unit 620 may determine up/down based on the change in the speed, that is, determine a point at which speed is increased as a downhill road, and a point at which speed is decreased as an uphill road. In addition, the altitude estimation unit 620 may also determine up/down based on the slope of the graph indicating the change in the acceleration, that is, determine a point at which the acceleration graph is changed in a positive direction as a downhill road, and a point at which the acceleration graph is changed in a negative direction as an uphill road. Moreover, the altitude estimation unit 620 may estimate the size of a slope from the size of the acceleration. For example, the altitude estimation unit 620 may estimate that a road is a downhill road with a steep movement route as acceleration in a positive direction is large, or a road is an uphill road with a steep movement route as acceleration in a negative direction is large.

Figure 9:
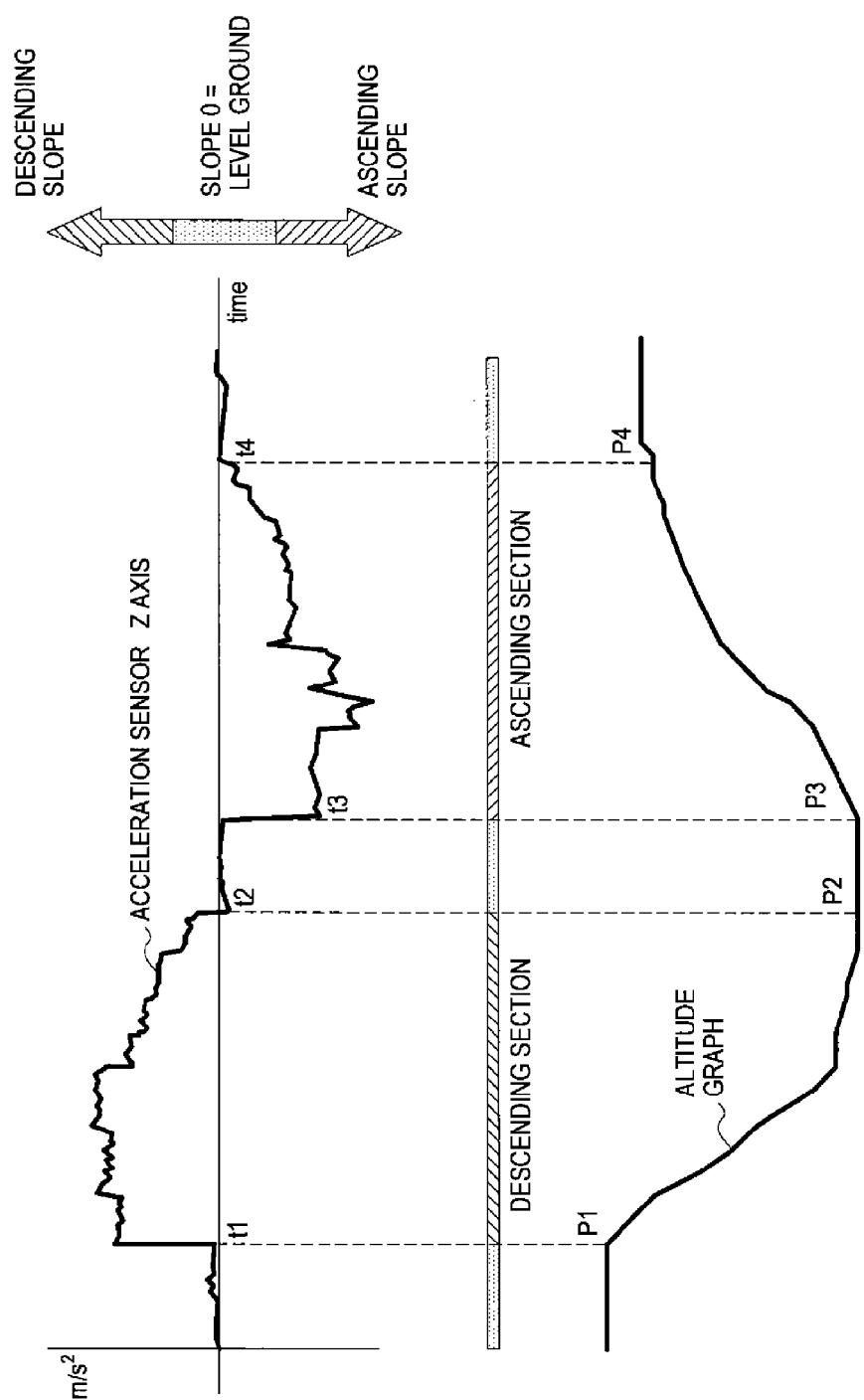
FIG. 9 is a diagram in which a graph indicating a change in acceleration has been associated with an altitude graph indicating up/down determined based on the graph.

Hereinafter, the up/down determination based on the slope of the graph indicating the change in the acceleration will be described with reference to FIG. 9 in which a graph indicating a change in acceleration in a Z direction has been associated with an altitude graph indicating up/down determined based on the graph. Since it is determined that a movement route from t1 to t2 of the acceleration graph illustrated at an upper part of FIG. 9 has a descending slope because acceleration has a positive value, a movement route from a point P1 to a point P2 corresponding to the altitude graph illustrated at a lower part of FIG. 9 is determined as a downhill road. Furthermore, a change in a slope in the downhill road is also estimated based on a change in the size of the acceleration as illustrated at the lower part of FIG. 9. Furthermore, since it is determined that a movement route from t2 to t3 of the acceleration graph illustrated at the upper part of FIG. 9 has a slope of 0 because acceleration is small, a movement route from the point P2 to a point P3 corresponding to the altitude graph illustrated at the lower part of FIG. 9 is determined as a flat route. Furthermore, since it is determined that a movement route from t3 to t4 of the acceleration graph illustrated at the upper part of FIG. 9 has an ascending slope because acceleration has a negative value, a movement route from the point P3 to a point P4 corresponding to the altitude graph illustrated at the lower part of FIG. 9 is determined as an uphill road. Furthermore, a change in a slope in the uphill road is also estimated based on the change in the size of the acceleration as illustrated at the lower part of FIG. 9.

Returning to FIG. 8, the up/down determination method based on the information acquirable from the sensor type "gyro" will be described. The information acquirable from the sensor type "gyro" includes the angular velocity data around the Z axis detected by the Z axis gyro sensor 114 provided in the navigation terminal 10-1, and the angular velocity data around the Y axis detected by the Y axis gyro sensor 115 as described above. Thus, the altitude estimation unit 620 determines up/down based on a change in the angular velocity data, and calculates a correction value of a point with up/down. For example, when a change in angular velocity is large, the altitude estimation unit 620 may determine up/down, that is, determine that a road is an uphill road because it is estimated that a user pedals the bicycle and the body of the bicycle is shaken. Meanwhile, when the change in the angular velocity is small, the altitude estimation unit 620 may determine up/down, that is, determine that a road is a downhill road because it is estimated that the body of the bicycle is stable.

Furthermore, the information acquirable from the sensor type "geomagnetic sensor" illustrated in FIG. 8 includes the azimuth data indicating the azimuth of the navigation terminal 10-1, which has been calculated by the azimuth calculation section 142 based on the geomagnetic data detected by the geomagnetic sensor 117 provided in the navigation terminal 10-1, as described above. Thus, the altitude estimation unit 620 determines up/down based on a change in the azimuth, and calculates a correction value of a point with up/down. For example, when a change in the azimuth is large, the altitude estimation unit 620 may determine up/down, that is, determine that a road is an uphill road because it is estimated that a user pedals the bicycle and the body of the bicycle is shaken. Meanwhile, when the change in the azimuth is small, the altitude estimation unit 620 may determine up/down, that is, determine that a road is a downhill road because it is estimated that the body of the bicycle is stable.

In addition, the altitude estimation unit 620 may also estimate the size of a slope from a periodical change in information acquired by the acceleration sensor, the gyro sensor, the geomagnetic sensor, and the like. For example, a cycle at which a user pedals the bicycle on an uphill road or the degree of shaking of the body of the bicycle when the user pedals the bicycle are considered to depend on the slope of the uphill road. In further detail, the cycle at which the user pedals the bicycle is increased as the slope of the uphill road is steep, and the degree of the shaking of the body of the bicycle when the user pedals the bicycle are considered to increase as the slope of the uphill road is steep. Therefore, the altitude estimation unit 620 may also estimate the size of the slope based on the cycle, the size of the amplitude and the like of the information acquired by the acceleration sensor, the gyro sensor, the geomagnetic sensor, and the like. Here, when a well-known relation is established between a periodical change in the information acquired by the acceleration sensor, the gyro sensor, the geomagnetic sensor, and the like and the size of the slope, the altitude estimation unit 620 may also estimate the size of the slope through the pattern matching of the periodical change.

Furthermore, the information acquirable from the sensor type "barometric pressure sensor" illustrated in FIG. 8 includes the height data indicating the height of the navigation terminal 10-1, which has been calculated by the height calculation section 144 based on the barometric pressure data detected by the barometric pressure sensor 118 provided in the navigation terminal 10-1, as described above. Thus, the altitude estimation unit 620 determines up/down based on the height data, and calculates a correction value of a point with up/down.

As described above, the altitude estimation unit 620 determines the up/down based on the information of various sensors, and calculates the correction value of a point with up/down. Here, the altitude estimation unit 620 may use only one sensor, or may also use a combination of some of the various sensors. Furthermore, the altitude estimation unit 620 may improve the accuracy of estimation by learning sensor information acquired at a point (for example, a point at which a correct altitude has been manually input) from which a correct altitude has been acquired. For example, when a change in newly acquired sensor information is matched with a change in sensor information around the point from which the correct altitude has been acquired, and the two changes coincide with each other or are similar to each other, the altitude estimation unit 620 may also estimate that a slope around the point from which the sensor information has been newly acquired coincides with or is similar to a slope around the point from which the correct altitude has been acquired. Then, the altitude estimation unit 620 outputs the calculated correction value of the point to the altitude correction unit 630.

The altitude correction unit 630 extracts altitude data of a section, which has been determined to have up/down by the altitude estimation unit 620, from the storage unit 640. Then, the altitude correction unit 630 compares the extracted altitude data with the correction value calculated by the altitude estimation unit 620, and corrects the altitude data based on the correction value when there is a difference therebetween. For example, the altitude correction unit 630 may replace the altitude data with the correction value, or may also correct the altitude data into a value between the altitude data and the correction value.

The storage unit 640 is a storage medium for storing a program for operating the altitude estimation server 60, the map data 641, the altitude data 642, and the like. In addition, the storage unit 640, for example, may also be a storage medium such as a nonvolatile memory including a flash ROM (or a flash memory), an EEPROM, an EPROM and the like, a magnetic disk including a hard disk, a disk-type magnetic disk and the like, an optical disc including a CD, a DVD-R, a BD (a registered trademark) and the like, or an MO disc.

(Operation Process)

Figure 10:
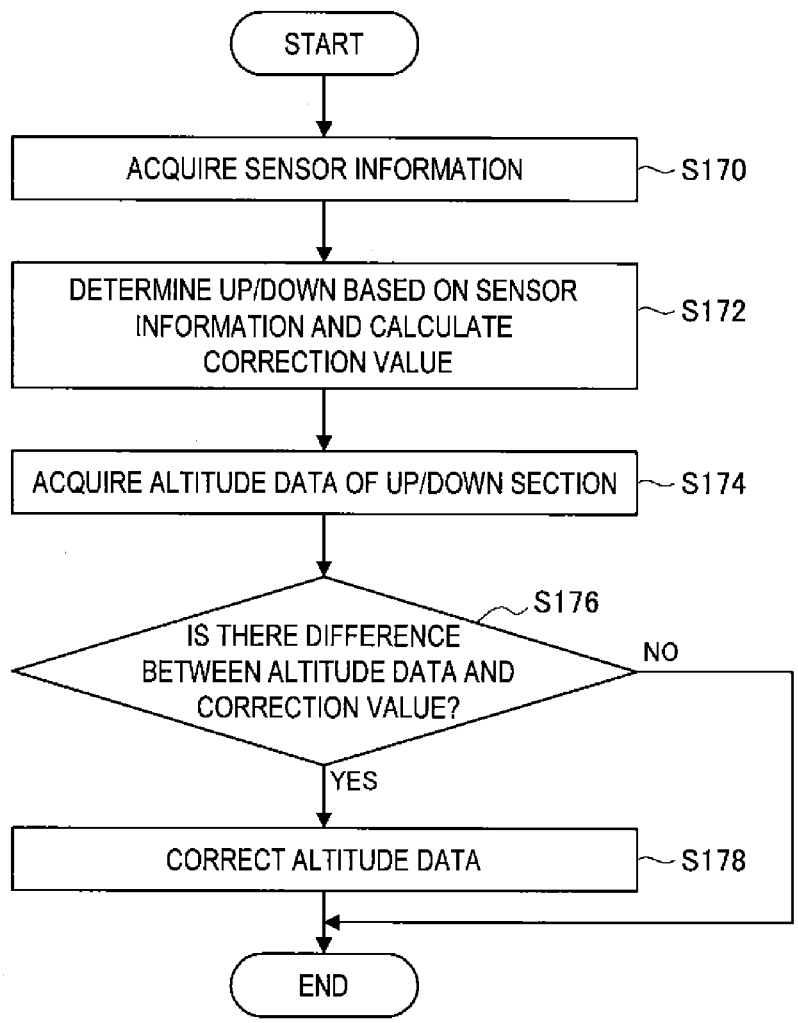
FIG. 10 is a flowchart illustrating an operation process of the altitude estimation server according to the first embodiment of the present disclosure.

Next, the operation process of the altitude estimation server 60 will be described with reference to FIG. 10. FIG. 10 is a flowchart illustrating the operation process of the altitude estimation server 60 according to the present embodiment. As illustrated in FIG. 10, in step S170, the altitude estimation unit 620 acquires information of various sensors from the communication unit 610 having received the information of the various sensors from the navigation terminal 10-1.

In step S172, the altitude estimation unit 620 determines up/down of altitude based on the acquired sensor information, and calculates a correction value for correcting the altitude of a point with up/down. The altitude estimation unit 620 outputs an up/down determination result and the correction value to the altitude correction unit 630.

In step S174, the altitude correction unit 630 acquires altitude data of an up/down section from the storage unit 640 according to the up/down determination result which is output from the altitude estimation unit 620.

In step S176, the altitude correction unit 630 compares the altitude data acquired from the storage unit 640 with the correction value output from the altitude estimation unit 620. When there is a difference between the altitude data and the correction value, the procedure proceeds to step S178. Meanwhile, when there is no difference between the altitude data and the correction value, the procedure ends.

In step S178, the altitude correction unit 630 corrects the altitude data based on the correction value. For example, the case of correcting the altitude of the bridge built across the river as illustrated in FIG. 4 will be described. First, the altitude estimation unit 620 of the altitude estimation server 60, for example, calculates a correction value at the center position of the bridge based on information detected by the sensor of the navigation terminal 10-1 attached to the bicycle 50 when the bicycle 50 has run along the bridge, and outputs the calculated correction value to the altitude correction unit 630. The altitude correction unit 630 compares the correction value output from the altitude estimation unit 620 with the altitude data of the bridge acquired from the storage unit 640. When there is an altitude difference as illustrated in FIG. 4, the altitude correction unit 630, for example, replaces altitude data at the center position of the bridge with the correction value, and corrects the altitude data. In this way, the altitude data corrected by the altitude estimation server 60 is used for route guidance, so that the navigation terminal 10-1 can display a bridge with up/down having an arch shape, similarly to an actual bridge, on the 3D map screen, or display an altitude graph with the up/down having an arch shape on the altitude screen.

As described above, in accordance with the navigation system according to the first embodiment, the altitude estimation server 60 estimates an altitude value based on the sensor information acquired from the navigation terminal 10-1 and corrects altitude data, resulting in the improvement of the accuracy of the altitude data. In addition, the altitude estimation server 60 may acquire sensor information from a plurality of navigation terminals 10-1, and correct altitude data. In this case, the altitude estimation server 60, for example, may compare an average value of correction values in the sensor information with altitude data, and replace the altitude data with the average value when there is an altitude difference therebetween. Furthermore, the plurality of navigation terminals 10-1 are connected to the altitude estimation server 60, resulting in the sharing of altitude data with high accuracy among the plurality of navigation terminals 10-1.

2. SECOND EMBODIMENT

Next, an altitude estimation apparatus according to the second embodiment of the present disclosure will be described. In the second embodiment of the present disclosure, the altitude estimation apparatus is applied to a navigation terminal 10-2. Furthermore, the navigation terminal 10-2 is realized by a personal navigation device (PND). Hereinafter, the configuration of the navigation terminal 10-2 according to the present embodiment will be described with reference to FIG. 11.

Figure 11:
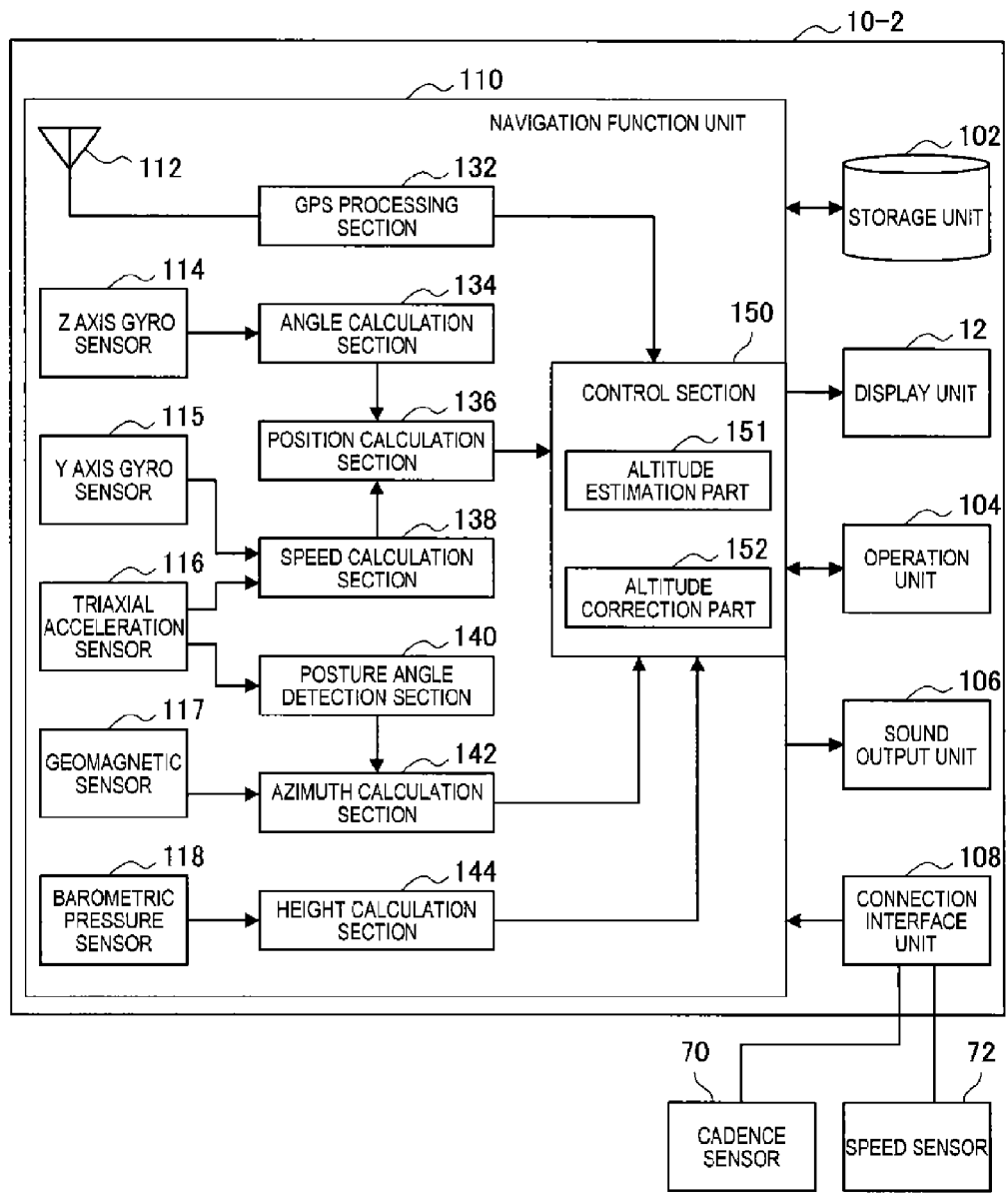
FIG. 11 is a block diagram illustrating a configuration of a navigation terminal according to a second embodiment of the present disclosure.

FIG. 11 is a block diagram illustrating a configuration of the navigation terminal 10-2 according to the present embodiment. As illustrated in FIG. 11, the navigation terminal 10-2 mainly includes a display unit 12, a storage unit 102, an operation unit 104, a sound output unit 106, a connection interface unit 108, and a navigation function unit 110.

The navigation function unit 110 includes a GPS antenna 112, a Z axis gyro sensor 114, a Y axis gyro sensor 115, a triaxial acceleration sensor 116, a geomagnetic sensor 117, a barometric pressure sensor 118, a GPS processing section 132, an angle calculation section 134, a position calculation section 136, a speed calculation section 138, a posture angle detection section 140, an azimuth calculation section 142, a height calculation section 144, and a control section 150.

Hereinafter, the configuration of the navigation terminal 10-2 will be described.

The storage unit 102 is a storage medium for storing a program for operating the navigation terminal 10-2, altitude data, map data and the like.

The control section 150 includes an altitude estimation unit 151 and an altitude correction unit 152. The altitude estimation unit 151 determines up/down based on information of various sensors, and calculates a correction value of a point with up/down, similarly to the altitude estimation unit 620 according to the first embodiment. Furthermore, the altitude correction unit 152 compares the correction value calculated by the altitude estimation unit 151 with the altitude data acquired from the storage unit 102, and corrects the altitude data when there is an altitude difference, similarly to the altitude correction unit 630 according to the first embodiment.

Since other configurations are the same as the configuration described with reference to FIG. 5, detailed description thereof will be omitted.

As described above, in accordance with the navigation terminal 10-2 according to the second embodiment, the altitude estimation unit 151 estimates an altitude value based on information detected by the sensors of the navigation terminal 10-2 during the travel, and altitude data is corrected by the altitude correction unit 152, resulting in the improvement of the accuracy of the altitude data stored in the navigation terminal 10-2.

3. THIRD EMBODIMENT

Application Example to Cellular Phone

Next, an altitude estimation apparatus according to the third embodiment of the present disclosure will be described. In the third embodiment of the present disclosure, the altitude estimation apparatus is applied to a navigation terminal 10-3 operable as a cellular phone terminal.

Figure 12:
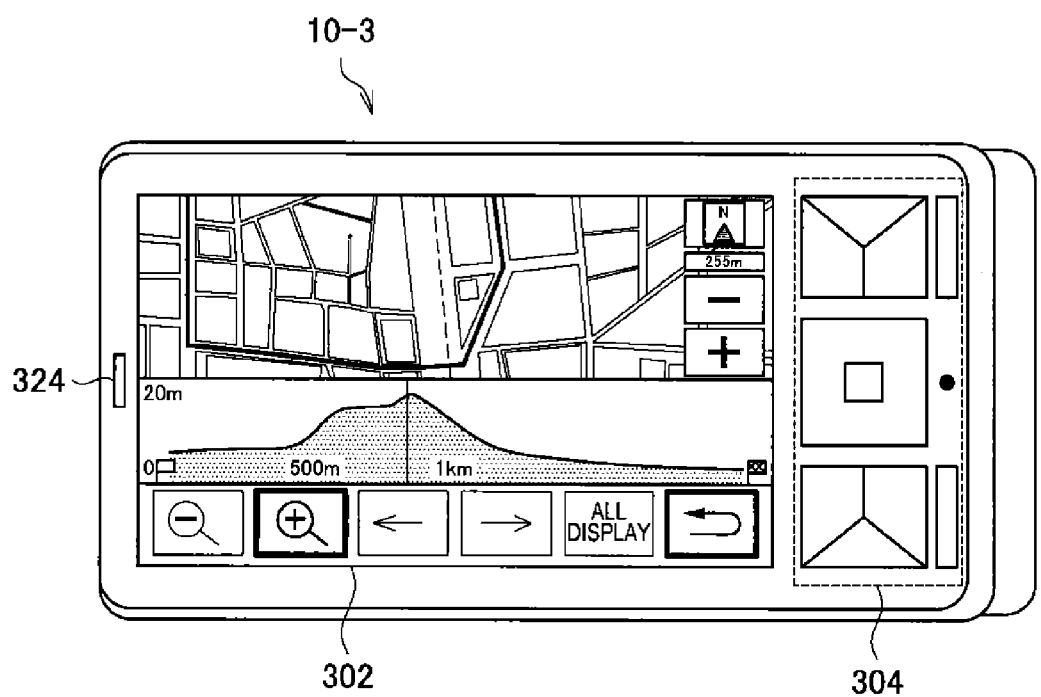
FIG. 12 is a diagram illustrating an external appearance of a navigation terminal according to a third embodiment of the present disclosure.

FIG. 12 is a diagram illustrating an external appearance of the navigation terminal 10-3 that displays a route guidance screen generated from altitude data and map data. As illustrated in FIG. 12, the navigation terminal 10-3 is realized by a cellular phone terminal, and mainly includes a display unit 302, an operation unit 304, and a speaker 324. Furthermore, the navigation terminal 10-3 may be attached to the bicycle 50 through a cradle, similarly to the navigation terminal 10-1.

Figure 13:
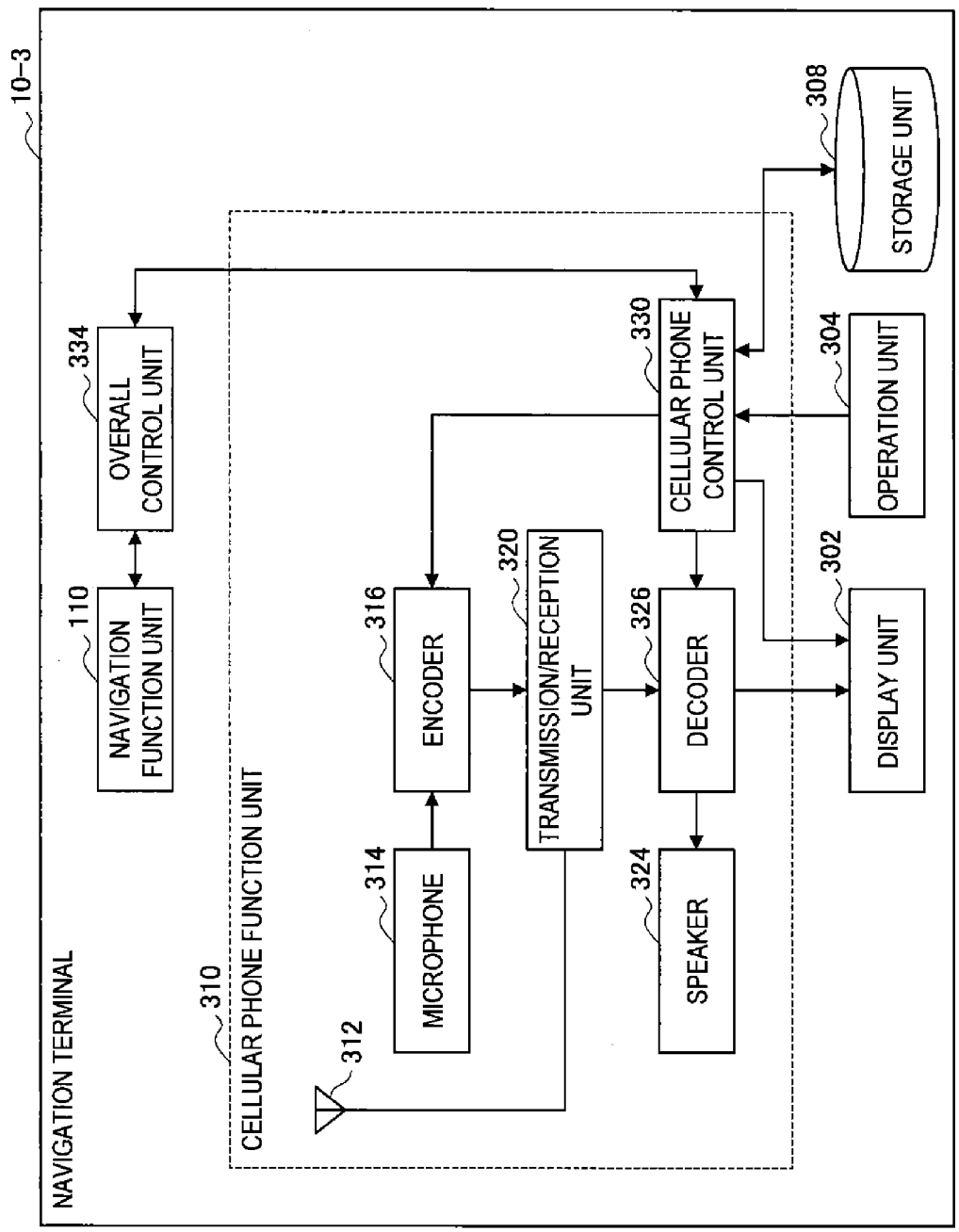
FIG. 13 is a block diagram illustrating a configuration of the navigation terminal according to the third embodiment of the present disclosure.

Hereinafter, the configuration of the navigation terminal 10-3 will be described with reference to FIG. 13. FIG. 13 is a block diagram illustrating a configuration of the navigation terminal 10-3 according to the present embodiment. As illustrated in FIG. 13, the navigation terminal 10-3 mainly includes a navigation function unit 110, a display unit 302, an operation unit 304, a storage unit 308, a cellular phone function unit 310, and an overall control unit 334.

The cellular phone function unit 310 is connected to the display unit 302, the operation unit 304, and the storage unit 308. In addition, FIG. 13 schematically illustrates the navigation terminal 10-3. However, the display unit 302, the operation unit 304, and the storage unit 308 are also connected to the navigation function unit 110. Since a detailed configuration of the navigation function unit 110 has been described in detail with reference to FIG. 5, description thereof will be omitted.

The cellular phone function unit 310 is provided to perform a call function, an electronic mail function and the like, and includes a communication antenna 312, a microphone 314, an encoder 316, a transmission/reception unit 320, a speaker 324, a decoder 326, and a cellular phone control unit 330.

The microphone 314 collects sound and outputs a sound signal. The encoder 316 performs digital conversion, encoding and the like with respect to the sound signal which is input from the microphone 314, and outputs sound data to the transmission/reception unit 320 under the control of the cellular phone control unit 330.

The transmission/reception unit 320 modulates the sound data, which is input from the encoder 316, according to a predetermined scheme, and transmits modulated data to a base station of a cellular phone through the communication antenna 312 in a wireless manner. Furthermore, the transmission/reception unit 320 demodulates a radio signal received in the communication antenna 312 to acquire sound data, and outputs the sound data to the decoder 326.

The decoder 326 performs decoding, analog conversion and the like with respect to the sound data which is input from the transmission/reception unit 320, and outputs a sound signal to the speaker 324 under the control of the cellular phone control unit 330. The speaker 324 outputs sound based on the sound signal supplied from the decoder 326.

Furthermore, when an electronic mail is received, the cellular phone control unit 330 supplies received data to the decoder 326 from the transmission/reception unit 320, and allows the decoder 326 to decode the received data. Then, the cellular phone control unit 330 outputs electronic mail data acquired through the decoding to the display unit 302 such that the electronic mail data is displayed on the display unit 302, and records the electronic mail data on the storage unit 308.

Furthermore, when an electronic mail is transmitted, the cellular phone control unit 330 allows electronic mail data input through the operation unit 304 to be encoded by the encoder 316, and transmits the encoded data through the transmission/reception unit 320 and the communication antenna 312 in a wireless manner.

The overall control unit 334 controls the above-mentioned cellular phone function unit 310 and the navigation function unit 110. For example, when an incoming call is received while the navigation function unit 110 is performing a navigation function, the overall control unit 334 temporarily switches the navigation function to a call function to be performed by the cellular phone function unit 310. After the call ends, the overall control unit 334 may allow the navigation function unit 110 to resume the navigation function.

4. CONCLUSION

As described above, in accordance with the altitude estimation apparatus according to the present disclosure, an altitude value is estimated based on information detected by the sensor during the travel and altitude data is corrected, resulting in the improvement of the accuracy of the altitude data. Consequently, it is possible to reduce the difference between the slope of an actual movement route and altitude information displayed on the navigation terminal 10, and to improve the accuracy of route search according to the slope of the movement route.

It should be understood by those skilled in the art that various modifications, combinations, sub-combinations and alterations may occur depending on design requirements and other factors insofar as they are within the scope of the appended claims or the equivalents thereof.

For example, each step in the process of the altitude estimation server 60 set forth in the present specification are not necessarily processed in time series in the sequence set forth as the flowchart illustrated in FIG. 10. For example, each step in the process of the altitude estimation server 60 may be performed in a sequence different from the sequence set forth as the flowchart, or may be performed in a parallel manner.

Furthermore, hardware, such as a central processing unit (CPU), a ROM, a random access memory (RAM) and the like embedded in the navigation terminal 10-1, the altitude estimation server 60, the navigation terminal 10-2, and the navigation terminal 10-3, may also be created by a computer program for exhibiting functions equivalent to those of the above-mentioned elements of the navigation terminal 10-1, the altitude estimation server 60, the navigation terminal 10-2, and the navigation terminal 10-3. Furthermore, a recording medium having recorded the computer program is also provided. The recording medium, for example, includes a magnetic disk, an optical disc, a magneto-optical disc, a flash memory and the like. Furthermore, the computer program, for example, may be delivered through a network without using a recording medium. Furthermore, the functional blocks illustrated in the functional block diagrams of FIG. 5, FIG. 7, FIG. 11, and FIG. 13 are configured by hardware, so that it is possible to perform a series of processes through the hardware.

Additionally, the present technology may also be configured as below.

(1) An information processing apparatus comprising: a processor that acquires estimated altitude data corresponding to a position based on detection information detected by a sensor at or near the position; and corrects altitude data associated with the position based on the estimated altitude data.

(2) The information processing apparatus of (1), further comprising: an interface that receives the detection information from another information processing apparatus.

(3) The information processing apparatus of (1), further comprising: an interface controlled by the processor to transmit the corrected altitude data to an information processing apparatus remote from the information processing apparatus.

(4) The information processing apparatus of (1), wherein the detection information is acceleration data detected by an acceleration sensor at or near the position.

(5) The information processing apparatus of (4), wherein the processor estimates the altitude data based on a change of the acceleration data over time.

(6) The information processing apparatus of (5), wherein the processor estimates the altitude to be higher when the change of the acceleration data indicates a decrease in acceleration, and estimates the altitude to be lower when the when the change of the acceleration data indicates an increase in acceleration.

(7) The information processing apparatus of (1), wherein the detection information is angular velocity data.

(8) The information processing apparatus of (7), wherein the processor estimates the altitude data based on a change of the angular velocity data over time.

(9) The information processing apparatus of (8), wherein the processor estimates the altitude to be higher when the change of angular velocity indicates an increase in angular velocity, and estimates the altitude to be lower when the change of angular velocity indicates a decrease in angular velocity.

(10) The information processing apparatus of (1), wherein the detection information is azimuth data detected by a geomagnetic sensor at or near the position.

(11) The information processing apparatus of (10), wherein the processor estimates the altitude data based on a change of the azimuth data over time.

(12) The information processing apparatus of (11), wherein the processor estimates the altitude to be higher when the azimuth data indicates a large change in azimuth over time, and estimates the altitude to be lower when the azimuth data indicates a small change in azimuth over time.

(13) The information processing apparatus of (1), wherein the information processing apparatus is a personal navigation device.

(14) The information processing apparatus of (13), further comprising:
a display; and a speaker, wherein the processor is configured to control the display to display navigation information and control the speaker to output audible instructions based on the corrected altitude data.

(15) The information processing apparatus of (1), wherein the information processing device is a mobile phone terminal, and the processor switches the mobile phone terminal between a navigation mode and a calling mode.

(16) An information processing apparatus comprising:
a processor that estimates altitude data corresponding to a position based on detection information detected by a sensor at or near the position; and computes altitude correction information associated with the position based on the estimated altitude data.

(17) An information processing apparatus comprising: a processor that determines a position of the information processing apparatus; a sensor that detects detection information corresponding to the information processing apparatus; an interface that transmits the position and the detection information to another information processing apparatus, which estimates altitude data corresponding to the position based on the detection information and corrects stored altitude data associated with the position based on the estimated altitude data.

(18) An information processing apparatus comprising: a processor that determines a position of the information processing apparatus; an interface that transmits the position to another information processing apparatus, and receives, from the another apparatus, altitude data corresponding to the position, the altitude data having been corrected based on estimated altitude data corresponding to the position, which was estimated based on detection information detected by a sensor at or near the position.

(19) An information processing system comprising: a first information processing apparatus including a processor that determines a position of the information processing apparatus; a sensor that detects detection information corresponding to the information processing apparatus; and an interface that transmits the position and the detection information to a second information processing apparatus; and a second information processing apparatus including a processor that estimates altitude data of the position based the detection information received from the first information processing apparatus, and corrects stored altitude data associated with the position based on the estimated altitude data.

(20) An information processing system comprising: a first information processing apparatus including a processor that determines a position of the information processing apparatus; and a first interface that transmits the position to a second information processing apparatus; and a second information processing apparatus including a processor that estimates altitude data corresponding to the position based on detection information detected by a sensor at or near the position, and corrects altitude data associated with the position based on the estimated altitude data; and a second interface that that transmits the corrected altitude data associated with the position to the first information processing apparatus.

Furthermore, the present technology may also be configured as below.

(1) An altitude estimation apparatus including:
an estimation unit that estimates altitude data of a position on a movement route using detection information detected by sensors on the movement route; and
a correction unit that corrects altitude data, which has been set to be associated with the position on the movement route, based on the altitude data estimated by the estimation unit.

(2) The altitude estimation apparatus according to (1), further including:
a reception unit that receives the detection information from a plurality of mobile terminals, the detection information being detected by the sensors of the plurality of mobile terminals,
wherein the estimation unit estimates the altitude data of the position on the movement route based on the detection information received from the plurality of mobile terminals in relation to the movement route.

(3) The altitude estimation apparatus according to (1) or (2), further including:
a storage unit that stores altitude data set to be associated with each position,
wherein, when the altitude data estimated by the estimation unit is different from the altitude data of the position on the movement route, which is stored in the storage unit, the correction unit corrects the altitude data stored in the storage unit.

(4) The altitude estimation apparatus according to any one of (1) to (3), further including:
a transmission unit that transmits the altitude data stored in the storage unit to the mobile terminal.

(5) The altitude estimation apparatus according to any one of (1) to (4), wherein the estimation unit estimates a change in altitude of the movement route based on a periodical change in the detection information, and estimates altitude data based on an estimation result of the change in altitude.

(6) The altitude estimation apparatus according to (5), wherein the estimation unit estimates the change in altitude of the movement route based on a size of amplitude or a length of a cycle of the detection information.

(7) The altitude estimation apparatus according to (1), further including:
the sensor; and
a storage unit that stores altitude data set to be associated with each position, wherein, when the altitude data estimated by the estimation unit is different from the altitude data of the position on the movement route, which is stored in the storage unit, the correction unit corrects the altitude data of the movement route stored in the storage unit.

(8) The altitude estimation apparatus according to (7), wherein the estimation unit estimates a change in altitude based on a periodical change in the detection information, and estimates altitude data based on an estimation result of the change in altitude.

(9) The altitude estimation apparatus according to (8), wherein the estimation unit estimates the change in altitude of the movement route based on a size of amplitude or a length of a cycle of the detection information.

(10) The altitude estimation apparatus according to any one of (7) to (9), further including:
a display control unit that controls display of a slope of the movement route based on the altitude data stored in the storage unit.

(11) The altitude estimation apparatus according to any one of (7) to (10), further including:
a navigation function unit that performs navigation using the altitude data stored in the storage unit.

(12) An altitude estimation method including:
estimating altitude data of a position on a movement route based on detection information regarding altitude of the movement route, the detection information being detected by sensors on the movement route; and
correcting altitude data, which has been set to be associated with the position on the movement route, based on the estimated altitude data.

(13) A program that causes a computer to serve as
an altitude estimation unit that estimates altitude data of a position on a movement route based on detection information regarding altitude of the movement route, the detection information being detected by sensors on the movement route, and
a correction unit that corrects altitude data, which has been set to be associated with the position on the movement route, based on the altitude data estimated by the altitude estimation unit.

REFERENCE SIGNS LIST 10-1, 10-2, 10-3 navigation terminal
102 storage unit
12 display unit
104 operation unit
106 sound output unit
108 connection interface unit
109 communication unit
110 navigation function unit
112 GPS antenna
114 Z axis gyro sensor
115 Y axis gyro sensor
116 triaxial acceleration sensor
117 geomagnetic sensor
118 barometric pressure sensor
132 GPS processing section
134 angle calculation section
136 position calculation section
138 speed calculation section
140 posture angle detection section
142 azimuth calculation section
144 height calculation section
150 control section
151 altitude estimation unit
152 altitude correction unit
40 network
50 bicycle
60 altitude estimation server
610 communication unit
620 altitude estimation unit
630 altitude correction unit
640 storage unit
641 map data
642 altitude data

The invention claimed is:

1. An information processing apparatus comprising:
circuitry configured to:
acquire estimated altitude data corresponding to a position based on detection information detected by a sensor at or near the position;
compare the estimated altitude data with an altitude data received from a storage unit to determine if there is a difference between the estimated altitude data and the altitude data; and
generate correction information based on the difference between the estimated altitude data and the altitude data,
wherein the detection information is acceleration data detected by an acceleration sensor at or near the position, and
wherein the circuitry estimates the altitude data based on a change of the acceleration data over time.

2. The information processing apparatus of claim 1, further comprising:
an interface that receives the detection information from another information processing apparatus.

3. The information processing apparatus of claim 1, further comprising:
an interface controlled by the circuitry to transmit the correction information to an information processing apparatus remote from the information processing apparatus.

4. The information processing apparatus of claim 1, wherein the circuitry is configured to estimate the altitude to be higher when the change of the acceleration data indicates a decrease in acceleration, and estimates the altitude to be lower when the change of the acceleration data indicates an increase in acceleration.

5. The information processing apparatus of claim 1, wherein the detection information is angular velocity data.

6. The information processing apparatus of claim 1, wherein the information processing apparatus is a personal navigation device.

7. The information processing apparatus of claim 6, further comprising:
a display; and
a speaker;
wherein the circuitry is configured to control the display to display navigation information and control the speaker to output audible instructions based on the correction information.

8. The information processing apparatus of claim 1, wherein the information processing device is a mobile phone terminal, and the circuitry switches the mobile phone terminal between a navigation mode and a calling mode.

9. An information processing apparatus comprising:
circuitry configured to:
acquire estimated altitude data corresponding to a position based on detection information detected by a sensor at or near the position;
compare the estimated altitude data with an altitude data received from a storage unit to determine if there is a difference between the estimated altitude data and the altitude data,
generate correction information based on the difference between the estimated altitude data and the altitude data,
wherein the detection information is angular velocity data, and
wherein the circuitry estimates the altitude data based on a change of the angular velocity data over time.

10. The information processing apparatus of claim 9, wherein the circuitry is configured to estimate the altitude to be higher when the change of angular velocity indicates an increase in angular velocity, and estimates the altitude to be lower when the change of angular velocity indicates a decrease in angular velocity.

11. An information processing apparatus comprising:
circuitry configured to:
acquire estimated altitude data corresponding to a position based on detection information detected by a sensor at or near the position;

compare the estimated altitude data with an altitude data received from a storage unit to determine if there is a difference between the estimated altitude data and the altitude data; and generate correction information based on the difference between the estimated altitude data and the altitude data, wherein the detection information is azimuth data detected by a geomagnetic sensor at or near the position.

12. The information processing apparatus of claim 11, wherein the circuitry is configured to estimate the altitude data based on a change of the azimuth data over time.

13. The information processing apparatus of claim 12, wherein the circuitry is configured to estimate the altitude to be higher when the azimuth data indicates a larger change in azimuth over time, and estimates the altitude to be lower when the azimuth data indicates a smaller change in azimuth over time.

14. The information processing apparatus of claim 1, wherein the circuitry is configured to compare the estimated altitude data with altitude data from a storage unit to obtain the corrected altitude data.

\* \* \* \* \*